United States Patent [19]

Harris et al.

[11] 4,203,968

[45] May 20, 1980

[54] COMBINATION VACCINE FOR SWINE DYSENTERY AND METHOD OF USE

[75] Inventors: Delbert L. Harris, Ames, Iowa; Robert A. Goodnow, Omaha, Nebr.; Robert D. Glock; Joann M. Kinyon, both of Ames, Iowa

[73] Assignees: Iowa State University Research Foundation, Inc., Ames, Iowa; Burns-Biotec Laboratories, Inc., Omaha, Nebr.

[21] Appl. No.: 16,623

[22] Filed: Mar. 1, 1979

Related U.S. Application Data

[62] Division of Ser. No. 935,000, Aug. 18, 1978, Pat. No. 4,152,414.

[51] Int. Cl.$^2$ ............................................... A61K 39/02
[52] U.S. Cl. ...................................................... 424/92
[58] Field of Search ............................................ 424/92

[56] References Cited

U.S. PATENT DOCUMENTS

| 4,152,413 | 5/1979 | Goodnow | 424/16 |
| 4,152,414 | 5/1979 | Harris et al. | 424/16 |
| 4,152,415 | 5/1979 | Harris et al. | 424/16 |

OTHER PUBLICATIONS

Hudson, M. J. et al., Res. Vet. Sci. 1976 21(3), 366–367, "Swine Dysentery, Protection of Pigs by Oral and Parentoral Immunization with Attenuated *Treponema hyodysenteriae*".

Harris, D. L. et al., J. Am. Vet. Med. Assoc. 172(4), 468–471, Feb. 1978, "Swine Dysentery, Studies of Onotobiotic Pigs Inoculated with *Treponema hyodysenteriae*, *Bacteroides vulgatus*, and *Fusobacterium Necrophorum*".

Primary Examiner—Shep K. Rose
Attorney, Agent, or Firm—Tilton, Fallon, Lungmus & Chestnut

[57] ABSTRACT

A combination vaccine for increasing the resistance of swine to dysentery infection comprises killed cells of a virulent isolate of *Treponema hyodysenteriae* in combination with concentrated killed cells of *Bacteroides vulgatus*, or *Fusobacterium necrophorum*, or mixtures thereof. This combination vaccine can be adapted for either oral or parenteral administration. For parenteral administration preferably only *Bacteroides vulgatus* is used in combination with *Treponema hyodysenteriae*. The oral vaccine is enteric-coated.

5 Claims, No Drawings

COMBINATION VACCINE FOR SWINE DYSENTERY AND METHOD OF USE

RELATED APPLICATION

This application is a division of our prior application entitled "Combination Vaccine for Swine Dysentery and Method of Use", Ser. No. 935,000, filed Aug. 18, 1978, now U.S. Pat. No. 4,152,414.

BACKGROUND AND PRIOR ART

An anaerobic spirochete, *Treponema hyodysenteriae*, has been characterized as the primary etiological agent in swine dysentery. Harris, D. L.; Glock, R. D.; Christensen, C. R.; and Kinyon, J. M.: *Vet. Med./Small Animal Clin.* 67:61 (1972); Taylor, D. J.; and Alexander, T. J. L.: *Brit. Vet. J.* 127:108 (1971). But relatively little is known about the immunology of swine dysentery although resistance to reinfection can be demonstrated in convalescent pigs. In 1976, Glock et al reported that parenteral vaccination of pigs with killed cells of a virulent isolate of *T. hyodysenteriae* provided a significant degree of protection against subsequent intragastric challenge with live virulent *T. hyodysenteriae*. Glock, R. D., Schwartz, K. J., and Harris, D. L., *Proceedings, International Pig Veterinary Society Congress*, June 1976, Ames, Iowa. The vaccine was given in six intravenous injections at 6-day intervals. This was the first reported success in immunizing swine against swine dysentery infection.

Hudson et al found that oral dosing of an attenuated strain of *T. hyodysenteriae* provided no protection against subsequent challenge. Hudson, M. J., Alexander, T. J. L., Lysons, R. J., Wellstead, P. D., *Brit. Vet. J.* (1974) 130:37. Subsequently, Hudson et al attempted to immunize pigs with live attenuated *T. hyodysenteriae* using a combination of oral dosing and parenteral inoculation. Hudson, M. J., Alexander, T. J. L., Lysons, R. J., Prescott, J. F., *Res. Vet. Science* (1976) 21:366. Oral doses were administered on three consecutive days, and after an interval of several days, intraperitoneal vaccinations were administered, which were followed after several more days with intramuscular vaccinations. The overall results of these tests were summarized as follows: "Although vaccination appeared to enhance immunity to swine dysentery, half of the vaccinated pigs developed the disease. This level of protection would be unlikely to be of practical value in the field."

*Treponema hyodysenteriae* is a true pathogen in the sense that in conventional pigs Koch's postulates have been fulfilled. Glock, R. D., and Harris, D. L., *Vet. Med./Small Animal Clin.* 67 (1972): 65–68; Kinyon, J. M., Harris, D. L. and Glock, R. D., *Infect. Immun.* 15 (1977): 638–646. The status of *T. hyodysenteriae* as a pathogen is further evidenced by the fact that herds of pigs exist which are free of swine dysentery and are also free of *T. hyodysenteriae*: Kinyon, J. M., Songer, J. G., Janc, M., and Harris, D. L., *In Proceedings 19th Annual Amer. Assoc. of Vet. Lab. Diag.* (1976): 65–74. By contrast, pigs from these same herds will develop signs and lesions of swine dysentery when orally inoculated with only *T. hyodysenteriae*. Kinyon, J. M., Harris, D. L., and Glock, R. D., *Infec. and Immun.* 15 (2), (1977): 638–646. However, *T. hyodysenteriae* appears to require elements of the normal colonic flora to exert its pathogenicity.

While swine dysentery infection can be reproduced in field-raised pigs by dosing them orally with pure cultures of *Treponema hyodysenteriae*, attempts to do so have failed until recently. In 1975, Meyer et al reported that swine dysentery was produced in gnotobiotic piglets by dosing them orally with *T. hyodysenteriae* together with 4 gram negative non-sporing rod-shaped anaerobes. Meyer, R. C., Simon, J., and Byerly, C. S., *Vet. Path.* 12, (1975): 46–54. The anaerobes were not specifically identified by Meyer et al, but they were tentatively designated as either species of Bacteroides or Fusobacteria. In further tests with gnotobiotic pigs, Harris et al found that lesions typical of acute swine dysentery were produced by intragastric inoculation of *T. hyodysenteriae* in combination with *Bacteroides vulgatus*, either alone or with *Fusobacterium necrophorum*. All bacteria were administered live. Harris, D. L., Alexander, T. J. L., Whipp, S. C., Robinson, I. M., Glock R. D., and Matthews, P. J., *J. Amer. Vet. Med. Assoc.* 172 (1978): 468–471. In field raised pigs, it would be expected that natural colonic flora would include *B. vulgatus*, *F. necrophorum* and similar bacteria so that *T. hyodysenteriae* can exert its pathogenicity, producing the swine dysentery infection.

SUMMARY OF INVENTION

Swine dysentery vaccines containing a combination of antigens prepared from *Treponema hyodysenteriae* and Bacteroides vulgatus have an enhanced action in increasing the resistance of swine to dysentery infection. More specifically, the combination vaccines of this invention contain concentrated killed cells of a virulent isolate of *Treponema hyodysenteriae* in combination with concentrated killed cells of *Bacterioides vulgatus*. From 0.25 to 2 parts by weight (dry basis) of the *Bacteroides vulgatus* cells should be present per part of the *T. hyodysenteriae* cells, and preferably from 0.5 to 1.5 parts of *Bacteroides vulgatus* cells per part of *T. hyodysenteriae*. This combination can be used in either an oral or a parenteral vaccine, and may be further adapted for intramuscular injection by including a suitable adjuvant.

For use as an oral vaccine, *Fusobacterium necrophorum* in the form of concentrated killed cells can be employed instead of or in addition to *Bacteroides vulgatus*. One preferred oral vaccine contains both *Bacteroides vulgatus* and *Fusobacterium necrophorum* cells with the *T. hyodysenteriae* antigen, and each are used in the relative proportions to *T. hyodysenteriae* specified above with respect to *B. vulgatus*.

The oral preparation is used in enteric-coated form. The enteric coating is selected so that it is resistant to dissolving in the swine stomach while dissolving in the swine intestines to release the antigenic cells for immunizing action. The enteric-coated oral vaccine may be used in conjunction with a parenteral vaccine prepared in accordance with the present invention. However, the combination oral and parenteral vaccines of this invention can also be employed separately.

For the most effective results, it is important to administer relatively large doses of the vaccines. For example, on the basis of the *T. hyodysenteriae* content at least 2 milligrams (dry basis) should be administered per parenteral dose and at least 3 mg. per oral dose. Similar amounts are preferably used when the animals are given both parenteral and oral inoculations. Both the parenteral and oral doses are preferably repeated. For example, two parenteral doses can be given with several days intervening between doses, and the oral doses can be repeated over several consecutive days.

DETAILED DESCRIPTION

The present invention can be practiced with any virulent isolate of *T. hyodysenteriae*. Attenuated or non-virulent isolates or strains are not desirable. A virulent isolate or strain is one which is capable of producing a typical swine dysentery infection. One suitable isolate has heretofore been identified in the literature as B204. See Kinyon, J. M., and Harris, D. L.: *Vet. Rec.* (1974): 95:219. Referred to in the same publication is the isolate identified as B234, which can also be used in practicing the present invention. However, type strain B78 (ATCC No. 27164) is not suitable, being non-virulent. Isolates B204 and B234 have been deposited with the American type Culture Collection; B204 being identified as ATCC No. 31212 and B234 as ATCC No. 31287. It should be understood that these isolates are representative of class of virulent isolates or strains which can be employed.

The *T. hyodysenteriae* cells for preparation of the vaccines can be cultured using trypticase soy broth (TSB) with 10% (v/v) fetal calf serum (FCS). For example, the inoculated broth can be incubated at 37°–38° C. under an anaerobic atmosphere, such as 50:50 $H_2:CO_2$ or $CO_2$ alone. The gaseous atmosphere should be deoxygenated. For further details, see Kinyon, J. M., and Harris, D. L.: Vet. Rec. (1974): 95:219.

For preparing vaccines in accordance with the present invention, it is believed that any strain or isolate of *Bacteroides vulgatus* or *Fusobacterium necrophorum* can be used. Strains of these bacteria which can be used in practicing the present invention are therefore readily available, such as those on deposit with the American Type Culture Collection, Rockville Maryland. For *B. vulgatus* these include the type strain ATCC No. 8482, and other strains or isolates, such as ATCC No. 31376.

For *F. necrophorum* the available strains include the ATCC reference strain No. 25286, and the strain identified by ATCC No. 27852. A strain of *B. vulgatus* employed in some of the experiments leading to the present invention, is identified as strain 28, and has been deposited with the American Type Culture Collection under ATCC No. 31376. Since neither *Bacteroides vulgatus* or *Fusobacterium necrophorum* are specific pathogens, there appears to be no difference for the purpose of the present invention between freshly isolated strains, and those which have been cultured in vitro for a large number of passages. However, if the synergistic antigenic action should be found to be lessened after prolonged in vitro cultivation, original cultures of the strains can be used, or freshly isolated strains can be obtained from the intestines of swine, where both *B. vulgatus* and *F. necrophorum* are normally present in field-raised pigs.

Standard media and culture techniques can be used for growing the *B. vulgatus* and *F. necrophorum*. For example, each bacterium can be grown separately in a standard pre-reduced anaerobically sterilized peptone-yeast extract media with added glucose. For example, 0.5% glucose can be added to the peptone-yeast broth. See Holdeman, L. V., Cato, E. P., and Moore, W. E. C.: *Anaerobe Laboratory Manual*, pp. 141–148, V.P.I. Anaerobe Laboratory, Blacksburg, Va. (4th ed. 1977). The cultures may be incubated under deoxygenated $CO_2$ at 37° C.

After the fermentation has been completed, the cells can be recovered and concentrated by centrifugation or ultrafiltration to obtain a cell slurry for further processing. The cells are killed by a suitable procedure, either in the fermenter or after recovery. Standard killing agents may be used such as formalin or merthiolate. For example, a killing-concentration of formalin, such as 0.2% formalin (v/v), can be added to the fermenter or to concentrated cell slurry. The killed cells of *T. hyodysenteriae*, *B. vulgatus*, and *F. necrophorum* are used to prepare the vaccines, the cells being concentrated and intermixed in the required proportions.

In general, *B. vulgatus* and *F. necrophorum* should be used in the vaccines in amounts of from 0.25 to 2 parts by weight on a dry cell basis per part of *T. hyodysenteriae*. For the oral vaccine, at least one of these bacteria should be present in the amount specified, and in a preferred embodiment, both of them are present in this amount. For the parenteral vaccine, the addition of only *B. vulgatus* is preferred. Killed cells of *F. necrophorum* may tend to produce undesirable side effects, such as abscesses, when injected intramuscularly or subcutaneously.

On the basis of present information, it appears that the preferred proportions of the additional bacteria (*B. vulgatus* and *F. necrophorum*) are within the range from 0.5 to 1.5 parts by weight (dry basis) per part of *T. hyodysenteriae*. Therefore, for the oral vaccine, at least one and preferably both of the added bacteria will be present in this amount, while the *B. vulgatus* cells will be used in this amount in the parenteral preparation.

Where the parenteral preparation is intended for intramuscular injection, it is not believed to be beneficial to use an adjuvant. However, for subcutaneous injection an adjuvant may have some value. For this purpose a meat-animal acceptable adjuvant, such as aluminum hydroxide, can be added. For example, aluminum hydroxide can be used at a final concentration in the injectable preparation of from 0.25 to 1% $Al_2O_3$.

The oral preparation should be enteric-coated. As used herein the term "enteric-coated" refers to a coating which is resistant to dissolving in the swine stomach while dissolving in the swine intestines. As disclosed in the co-pending application of Robert A. Goodnow, filed on even data herewith, entitled "Oral Vaccine for Swine Dysentery and Method of Use", such enteric coatings are preferably selected so that they are insoluble in water at a pH below 5.0 while being slowly soluble in water at a pH of 5.8 to 6.2.

Any of the known enteric coatings which meet these solubility or pH conditions can be utilized. One suitable coating material is cellulose acetate phthalate, which may be plasticized with diethyl or dibutyl phthalate so that the coating is more resistant to cracking. For application, the enteric coating material may be dissolved in a suitable volatile organic solvent, and the enteric coat may be built up in a series of applications to assure that the coating will be complete and relatively uniform. One well known procedure of this kind is referred to as the Open-Pan Ladle Coating Process. For example, 30 to 40 parts by weight of cellulose acetate phthalate together with 8 to 10 parts of diethyl phthalate may be dissolved in 250 to 300 parts by weight of acetone to form a coating solution for such application.

Suitable resins may also be used, such as acrylic resins prepared for use as enteric coatings. One such product is sold under the trademark "Eudragit L 90" by Röhm Pharma Gmbh, Darmstadt, West Germany. This enteric coating material, which is supplied in granular form containing 10% water. The release pH of Eudragit L can be increased where desired by mixing it with Eudragit S. The manufacturer describes Eudragit L as soluble in intestinal juice from pH 6.0 and Eudragit S as soluble from pH 7.0. Eudragit L and mixtures with Eudragit S are soluble in ethanol and acetone, which may be used for applying the coating. They may be plasticized, if needed with various plasticizers, such as polyethylene glycol, diethyl or dibutyl phthalate, triacetin, or castor oil. For example, from 70 to 90 parts by weight of Eudragit L can be combined with 20 to 30 parts by weight of diethyl phthalate. The Wurster Coating Process can also be used to apply the enteric coating. This process is described in U.S. Pat. Nos. 3,241,520 and 3,253,944. It is carried out as a commercially available service by Coating Place, Inc., Verona, Wisconsin.

The enteric-coated oral vaccine is preferably in the form of pellets or granules which can be readily mixed with swine feed material for administration to the animals. For example, such granules may range from about −20 mesh to +100 mesh (U.S. Standard Screen). The granules are mixed with a finely-divided feed material such as a ground feed used for pigs after weaning. Any swine or pig feed material can be used, such as basal ration containing ground corn, rolled oats, soybean meal, minerals and vitamins. The coated granules may also be premixed with vitamin-mineral fortification premixes, which are later combined with the other feed ingredients.

To act as a filler or bulk stabilizer for desiccation and pellet preparation, standard filler substances may be added to the cell slurry such as sucrose, dextrose, lactose, etc. In general, the amount of filler-stabilizer to be added may range from about 10 to 50 parts by weight of filler per 100 parts of cells (dry basis). Prior to the addition of the filler, the cell concentrate preferably contains in excess of 3.0 milligrams of cells (dry basis) per milliliter of slurry. For example, the cell concentrates may contain from about 4 to 7 milligrams of cells (dry basis) per milliliter of cell slurry. The particular concentration is not critical, since most of the residual water of the slurry is removed by a suitable drying procedure in preparing the pellets.

The mixed cell slurry containing the added binder may be dried by a suitable biological drying procedure such as freeze-drying. Preferably, the drying is carried out at a relatively low temperature, such as below 40° C. The dried material is then pulverized to a finely-divided condition for preparing tablets or granules.

For example, the mixed cell concentrates in the form of liquid slurries are mixed with sucrose and cellulose, and kneaded to a doughy consistency. The dough is then extruded in the form of noodles or ribbons, which are broken up and formed into granules. The granule size is not critical, but desirably is of a size smaller than 20 mesh (U.S. Standard Screen). The granules are dried in an oven at a relatively low temperature, such as 37° C. until most of the moisture has been removed. The final moisture content is not critical, and desirably may range from about 1 to 3% water by weight.

In applying tablet and granule coatings, a dye may be included as a colorant for the coating. This permits the coating to be more readily inspected for thickness and uniformity, and makes it easier to detect imperfections in the coatings. In practicing the present invention, it is desirable to use a dye in the enteric coatings of the present invention, although it is not essential with respect to the desired immunizing action. Suitable dyes include Lake Blue No. 2 and crystalline violet dye.

While the vaccines of the present invention may be applied to adult swine, such as breeding sows, an important use is with growing pigs. For example, the method may be applied to feeder pigs, starting at the age of about 3 to 8 weeks. The method may also be applied to older pigs during their growth period prior to marketing. The pigs raised under field conditions are highly subject to swine dysentery infection with consequent economic loss due to lowering of the rate of weight gain and the feed efficiency. By increasing the resistance of the pigs to swine dysentery infection, optimum rates of weight gain may be maintained.

In practicing the present invention, using either the oral vaccine, the parenteral vaccine, or both, the dose level can be related to the amount of *T. hyodysenteriae* administered. For example, with the oral preparations, it is desirable to administer at least 3 milligrams of the killed cells of *T. hyodysenteriae* (dry basis) per animal. Preferably, the doses are administered daily (once every 24 hours), such as by admixture of the enteric-coated granules with a feed material, and the dosing is continued for a period of at least five days, such as from 5 to 15 days. In a preferred embodiment, the oral doses contain at least 4 mg. of the *T. hyodysenteriae* cells (dry basis) per dose, such as doses in the range of 4 to 6 mg.

For the parenteral vaccine, it is preferred to inject at least 2 milligrams (dry basis) of *T. hyodysenteriae* cells per animal per dose. If necessary, the parenteral dose can be repeated, such as a total of from 2 to 3 doses. In a preferred embodiment, the parenteral dose may contain from 3 to 6 mg. (dry basis) of *T. hyodysenteriae* cells per dose.

Where the same animals are to be given both the oral and parenteral preparations, it is preferred to follow the dosing procedure described in the co-pending application of Delbert L. Harris and Robert A. Goodnow, filed on even date herewith, and entitled "Method of Increasing the Effectiveness of Oral Vaccination of Swine Dysentery". However, the oral and parenteral vaccines of this invention can also be used separately, or with a different administration procedure than described in the Harris and Goodnow application.

The invention is further illustrated by the following examples.

EXPERIMENTAL EXAMPLES

Materials and Methods

Experimental Animals—Pigs from a herd with no history of swine dysentery were placed in isolation units at approximately 8 weeks of age and fed a 16% protein grower ration which contained no drugs.

Preparation of Inoculum—Cultures of *Treponema hyodysenteriae* (isolate B204) were grown approximately 24 hours in aerobically prepared trypticase soy broth containing 10% fetal calf serum under deoxygenated $H_2:CO_2$ at 38° C. One hundred ml of whole culture was administered to each pig via stomach tube following a 48 hour starvation period. The isolate of *T. hyodysenteriae* had not been passaged more than 15 times in vitro.

Preparation of Vaccines—An oral vaccine and a parenteral vaccine were prepared containing *Treponema hyodysenteriae* isolate (B204, No. 31212) and *Bacteroides vulgatus* (Strain 28, ATCC No. 31376).

A. Preparation of *Treponema hyodysenteriae* Antigen

Growth:

The *T. hyodysenteriae* organism was grown in trypticase soy broth enriched with 10% fetal calf serum (Gibco, Grand Island, N.Y.) in a 28-liter pilot New Brunswick fermenter and grown to an average cell mass level of equal to or greater than $2.0 \times 10^9$ cells/ml. Seventy-two (72) liters of *T. hyodysenteriae* grown to 1.25 milligrams dry wt. antigen/ml of fermenter culture was used in this preparation.

Concentration:

The cell culture was inactivated with a 1:10,000 concentration Merthiolate. The cell mass was concentrated by forcing the cell mass through a 100,000 molecular weight size membrane by positive air pressure. The cell slurry was concentrated to a level of 30 milligrams dry wt. antigen/ml per 3.5 liters of slurry.

B. Preparation of *Bacteroides vulgatus* Antigen

The *B. vulgatus* organism was grown in standard peptone yeast extract glucose medium to a level of 2.3 milligrams dry wt. antigen/ml fermenter grown culture. Forty-five (45) liters of this cell culture was concentrated by similar ultrafiltration to a cell mass level of 34.7 milligrams dry wt. antigen/ml per 3 liters slurry.

C. Preparation of Combination Antigens

The 3.5 liters of *T. hyodysenteriae* slurry and 3.0 liters of *B. vulgatus* were combined in a common vessel. The slurry was concentrated by similar ultrafiltration to 2.85 liters of slurry.

D. Preparation of Enteric Coat on Vaccine

Carrier:

Twenty (20) mesh sucrose pariels were sprayed with the bacterial antigen slurry to a 15.97% antigen/product wt. increase. Drying temperatures were maintained between 102°-110° F. above the drying bed and between 144°-165° F. on the inlet slurry line. After the antigen was coated upon the sugar seeds, an enteric resin overcoat was sprayed on the antigen-sugar seeds.

E. Enteric Solution 83.3 Grams Eudragit L90, and 25 grams of diethyl phthalate was added to 1.0 liters of methanol. This solution was then q.s. to 1.67 liters with acetone. This solution was sprayed on the sugar-antigen carrier and air dried according to the Wurster Process. See U.S. Pat. Nos. 3,253,944 and 3,241,520. The Wurster coating process was performed by Coating Place, Inc., Verona, Wisconsin. One (1) liter of concentrated slurry resulted in 1 kilogram of oral swine dysentery vaccine.

EXPERIMENT 1

Thirty-four pigs were randomly assigned to individual isolation units. The pigs were immunized as follows:

| Group | No. of Pigs | Parenteral Vaccine Intramuscular | Parenteral Vaccine Intraperitoneal | Oral Vaccine |
|---|---|---|---|---|
| I | 9 | + | − | − |
| II | 9 | + | − | + |
| III | 8 | − | + | + |
| IV | 8 | − | − | − |

On day 0 the pigs were weighed individually and pigs in groups I, II, and III were injected with 5 ml/pig of the parenteral vaccine. Starting on day 9, the oral vaccine was fed to the pigs in groups II and III by mixing 1.0 gram of the vaccine in approximately 500 grams of feed which was spred across the floor for consumption by the pigs. Additional feed containing no vaccine was given later. The oral vaccine was administered daily through day 23. On day 14, the pigs in groups I, II, and III were injected with 5 ml/pig of the parenteral vaccine. On day 24, all pigs were weighed. Feed with withheld on days 24 and 25. On day 26, rectal swabs were collected and all pigs were challenged with *T. hyodysenteriae* ($8.0 \times 10^9$ organisms per pig).

EXPERIMENT 2

Forty-five pigs were randomly assigned to isolation units. The pigs were immunized as follows:

| Group | No. of Pigs | Parenteral Vaccine Intramuscular | Oral Vaccine |
|---|---|---|---|
| I | 8 | + | − |
| II | 9 | − | +* |
| III | 9 | + | +* |
| IV | 10 | + | +* (continuous) |
| V | 9 | C** | C** |

*Group II and III received oral vaccine daily until challenge; Group IV received oral vaccine daily before and after challenge.
**Received control placebo-no T. hyodysenteriae or B. vulgatus antigen.

On day 0 the pigs were weighed individually and pigs in groups I, III, and IV were injected with 5 ml/pig of parenteral vaccine. On day 8 the oral vaccine was initiated in groups II, III, and IV as described above. The oral vaccine was continued through day 28 for groups II and III. On day 15 the pigs in groups I, III, and IV were injected with 5 ml/pig of parenteral vaccine. On day 28 all pigs were weighed. Feed was withheld on days 29 and 30. On day 31, rectal swabs were collected and all pigs were challenged with *T. hyodysenteriae* ($9.0 \times 10^9$ organisms per pig).

Pigs were weighed at weekly intervals after challenge and rectal swabs were collected twice weekly. Clinical evaluation of response to challenge was recorded for each pig on a daily basis for 34 days post-inoculation (DPI).

Evaluation of Response to Challenge—Each pig was observed daily and 3 clinical parameters were scored on a scale of 1 to 4.

General Condition: 1=normal; 2=gaunt, mildly inactive; 3=very gaunt, rough hair, very inactive; 4=emaciated, moribund.

Feces Consistency: 1=normal, firm; 2=soft, not formed; 3=liquid; 4=watery.

Feces Composition: 1=normal; 2=increased mucus; 3=increased mucus, small flecks of blood; 4=large amount of blood present.

For purposes of tabulation, a score of 3 or 4 was considered to be respectively cachexia, diarrhea and dysentery in the 3 parameters observed.

A daily index for each pig was calculated as the mean of the scores for the 3 individual observations. Pigs that died were given the maximum score of 4 for each of the parameters through the remainder of the study for purposes of analysis.

Isolation of *T. hyodysenteriae*—A rectal swab was collected and placed in a culturette holder containing transport medium. The swab was held at 4° C. and inoculated onto selective medium for isolation of *T. hyodysenteriae* within 24 hours of collection. The selective medium contained trypticase soy agar, 5% bovine blood, and 400 mcg/ml of Spectinomycin sulfate and was incubated under 80% $H_2$ and 20% $CO_2$ with palladium catalysts at 42° C. The selective medium was examined at 2, 4, and 6 days of incubation and the presence or absence of pathogenic (βhemolytic) *T. hyodysenteriae* was recorded.

Necropsy Procedures—A necropsy was performed on all pigs that died during the trial. Macroscopic lesions were recorded and a swab was collected from the colonic mucosa for isolation of *T. hyodysenteriae*. Salmonella isolations were attempted from the mesenteric lymph node, small intestine and colon.

The data is set out below in Tables A, B, and C for Experiment 1 and Tables D, E, and F for Experiment 2.

RESULTS AND DISCUSSION

Exp. 1—Some pigs in all vaccinated groups (I, II, and III) showed symptoms of diarrhea and dysentery but of much less severity and duration than nonvaccinated control pigs (group IV). The incubation period of the disease was delayed in vaccinated pigs as compared to nonvaccinated pigs. Vaccinated pigs gained weight more rapidly and gained more total weight than nonvaccinated pigs.

*Treponema hyodysenteriae* was isolated from the feces of pigs in the nonvaccinated groups within 4 days post inoculation. By contrast, most vaccinated pigs did not shed *T. hyodysenteriae* until 14 days post inoculation. Vaccination did not stop the establishment of infection by *T. hyodysenteriae*.

One pig died in the nonvaccinated group due to swine dysentery. No pigs died in the vaccinated groups.

Exp. 2—The pigs in this study appeared to be more severely challenged than Exp. 1. Pigs in group III had less clinical signs of swine dysentery and performed better based on weight gains than pigs in group V (controls). Pigs in group IV were severely affected very early after challenge which may have been due to the continual exposure to the oral vaccine. By contrast, this was the only group in which no deaths occurred.

Seven pigs died during the study. Six of these pigs died of swine dysentery while one pig in group II died of necroproliferative enteritis.

TABLE A

Clinical Responses in Pigs Inoculated Intragastrically with *T. hyodysenteriae* Exp. 1

| Clinical response | Group | | | |
|---|---|---|---|---|
| | I N = 9[a] | II N = 9 | III N = 8 | IV N = 8 |
| Diarrhea: | | | | |
| Day of Onset[b] | 15.33 | 25.00 | 21.63 | 12.25 |
| Days Duration | 6.67 | 2.78 | 2.88 | 15.13 |
| No. Affected | 6 | 6 | 5 | 8 |
| Dysentery: | | | | |
| Day of Onset | 21.33 | 25.22 | 24.00 | 14.00 |
| Days Duration | 4.89 | 1.11 | 1.13 | 9.63 |
| No. Affected | 5 | 5 | 4 | 7 |
| Cachexia: | | | | |
| Day of Onset | 29.00 | 34.00 | 34.00 | 18.63 |
| Days Duration | 1.78 | 0 | 0 | 5.50 |
| No. Deaths | 0 | 0 | 0 | 1 |
| Combined Index | 1.46 | 1.25 | 1.27 | 1.97 |

[a]N equals number of pigs per group
[b]Study terminated at 34 days. Calculations are based on a value of 34 assigned to each pig which remained normal.

TABLE B

Cumulative Average Gain (pounds) per Pig Inoculated Intragastrically with *T. hyodysenteriae* Exp. 1

| Days Post inoculation | Group | | | |
|---|---|---|---|---|
| | I | II | III | IV |
| 7 | 6.66 | 6.00 | 5.75 | 3.00 |
| 14 | 11.33 | 15.00 | 12.25 | .25 |
| 21 | 20.11 | 23.11 | 20.25 | 9.36 |
| 28 | 29.33 | 28.45 | 26.12 | 18.07 |
| 35 | 40.00 | 39.56 | 35.75 | 25.07 |

TABLE C

Isolation of Pathogenic *T. hyodysenteriae* from the Feces of Pigs Inoculated Intragastrically with *T. hyodysenteriae* Exp. 1

| Days Post inoculation | Group | | | |
|---|---|---|---|---|
| | I | II | III | IV |
| 0 | 0/9[a] | 0/8 | 0/8 | 0/7 |
| 4 | 0/9 | 0/9 | 0/8 | 2/8 |
| 7 | 4/9 | 1/9 | 2/8 | 4/8 |
| 11 | 7/9 | 8/9 | ⅜ | 8/8 |
| 14 | 8/9 | 8/9 | 6/8 | 7/7 |
| 21 | 6/9 | 5/7 | ⅜ | 6/7 |
| 28 | ⅜ | 5/9 | ⅜ | 5/7 |

[a]Denominator equals number of pigs sampled. Numerator equals number of pigs positive.

TABLE D

Clinical Responses in Pigs Inoculated Intragastrically with *T. hyodysenteriae* Exp. 2

| Clinical Response | Group | | | | |
|---|---|---|---|---|---|
| | I N = 8[a] | II N = 9 | III N = 9 | IV N = 10 | V N = 9 |
| Diarrhea: | | | | | |
| Day of Onset[b] | 16.00 | 12.33 | 21.33 | 9.0 | 12.78 |
| Days Duration | 9.63 | 4.78 | 3.56 | 8.2 | 10.22 |
| No. Affected | 7 | 8 | 8 | 10 | 9 |
| Dysentery: | | | | | |
| Day of Onset | 16.00 | 13.22 | 21.78 | 8.9 | 13.00 |
| Days Duration | 6.38 | 4.78 | 2.44 | 6.5 | 8.67 |
| No. Affected | 7 | 8 | 8 | 10 | 9 |
| Cachexia: | | | | | |
| Day of Onset | 25.88 | 14.78 | 27.22 | 17.7 | 17.11 |
| Days Duration | 6.13 | 7.44 | 1.44 | 4.1 | 7.22 |
| No. Deaths | 1 | 2 | 2 | 0 | 2 |
| Combined Index | 1.78 | 1.64 | 1.39 | 1.64 | 1.91 |

[a]N equals number of pigs per group
[b]Study terminated at 35 days. Calculations are based on a value of 35 assigned to each pig which remained normal.

TABLE E

Cumulative Average Gain (pounds) per Pig Inoculated Intragastrically with *T. hyodysenteriae* Exp. 2

| Days Post inoculation | Group | | | | |
|---|---|---|---|---|---|
| | I | II | III | IV | V |
| 7 | −.12 | −1.00 | 6.22 | 3.10 | 3.56 |
| 14 | 2.25 | 1.53 | 5.89 | −5.60 | 5.28 |
| 21 | 4.68 | 3.03 | 10.00 | .10 | 1.35 |
| 28 | 11.54 | 6.36 | 17.00 | 5.90 | 7.07 |
| 35 | 16.68 | 18.50 | 21.97 | 11.80 | 13.64 |

TABLE F

Isolation of Pathogenic *T. hyodysenteriae* from the Feces of Pigs Inoculated Intragastrically with *T. hyodysenteriae* Exp. 2

| Days Post inoculation | Group | | | | |
|---|---|---|---|---|---|
| | I | II | III | IV | V |
| 0 | 0/8[a] | 0/9 | 0/9 | 0/10 | 0/9 |
| 4 | 2/8 | 1/9 | 1/9 | 3/10 | 0/9 |

TABLE F-continued

Isolation of Pathogenic *T. hyodysenteriae*
from the Feces of Pigs
Inoculated Intragastrically
with *T. hyodysenteriae* Exp. 2

| Days Post inoculation | I | II | III | IV | V |
|---|---|---|---|---|---|
| 7 | 6/8 | 4/9 | 0/9 | 9/10 | 5/9 |
| 11 | 2/8 | 6/8 | 5/9 | 9/10 | 7/9 |
| 14 | 4/8 | | 3/9 | 8/10 | 6/8 |
| 18 | 3/7 | 6/8 | 2/8 | 6/10 | 6/7 |
| 21 | 2/7 | 6/8 | 4/8 | 5/10 | 4/7 |
| 25 | 3/7 | 3/7 | | 1/10 | 2/7 |
| 28 | 2/7 | 4/7 | 4/8 | 0/10 | 4/7 |
| 32 | 0/7 | 0/7 | 0/7 | 0/10 | 0/7 |
| 35 | 0/7 | 2/7 | 0/7 | 0/10 | 0/7 |

*a*Denominator equals number of pigs sampled. Numerator equals number of pigs positive.

FURTHER EXAMPLES

Oral Preparation

*Treponema hyodysenteriae, Bacteroides vulgatus* and *Fusobacterium necrophorum* are each separately grown under anaerobic conditions, as previously described, to provide immunizing antigens for use in combination. Each culture after Merthiolate inactivation, is mixed together and concentrated by ultrafiltration to provide at least 30 mg/ml *T. hyodysenteriae*, 34.7 mg/ml *Bacteroides vulgatus* and 35.0 mg/ml *Fusobacterium necrophorum* in the wet mixed slurry. Enteric coated granules are then prepared.

The concentrated mixed antigen slurry is combined with the other ingredients in the following proportions:
1500 cc antigen slurry
11.5 kilo sucrose
3.5 kilo microcrystalline cellulose
0.2% dry weight Lake Blue No. 2 Dye
H₂0 added as needed for obtained proper texture Once this mixture is partially mixed the moistened mass of material is run through a commercial extruder at least three times to provide a uniform mix of antigen to carrier. The cylindrical pieces are then shaped into uniform beads in a manumerizer. The bead preparation is dried at least 1–8 hours leaving 1–3